(12) United States Patent
Kishawi et al.

(10) Patent No.: US 7,699,768 B2
(45) Date of Patent: Apr. 20, 2010

(54) DEVICE AND METHOD FOR NON-INVASIVE, LOCALIZED NEURAL STIMULATION UTILIZING HALL EFFECT PHENOMENON

(76) Inventors: Eyad Kishawi, 216 Barneson Ave., San Mateo, CA (US) 94402; Stephen J. Norton, 3500 Rock Creek Dr., Raleigh, NC (US) 27609

( * ) Notice: Subject to any disclaimer, the term of this patent is extended or adjusted under 35 U.S.C. 154(b) by 49 days.

(21) Appl. No.: 11/741,613

(22) Filed: Apr. 27, 2007

(65) Prior Publication Data
US 2007/0255085 A1  Nov. 1, 2007

Related U.S. Application Data (60) Provisional application No. 60/745,829, filed on Apr. 27, 2006.

(51) Int. Cl.
*A61N 2/00* (2006.01)
(52) U.S. Cl. ........................................................ 600/9
(58) Field of Classification Search ............... 600/9–15; 128/897, 899; 601/9
See application file for complete search history.

(56) References Cited

U.S. PATENT DOCUMENTS

| | | | |
|---|---|---|---|
| 3,735,756 A | 5/1973 | Richards et al. | |
| 4,121,594 A | 10/1978 | Miller et al. | |
| 4,940,453 A | 7/1990 | Cadwell | |
| 5,092,835 A | 3/1992 | Schurig et al. | |
| 5,476,438 A * | 12/1995 | Edrich et al. | 600/2 |
| 5,630,710 A | 5/1997 | Tune et al. | |
| 5,733,240 A | 3/1998 | De Visser | |
| 5,738,625 A * | 4/1998 | Gluck | 600/9 |
| 6,416,458 B1 * | 7/2002 | Spiegler | 600/9 |
| 6,645,144 B1 | 11/2003 | Wen et al. | |
| 2004/0143300 A1 | 7/2004 | Rogers | |
| 2005/0182288 A1 | 8/2005 | Zabara | |
| 2005/0249667 A1 | 11/2005 | Tuszynski et al. | |
| 2006/0211958 A1 * | 9/2006 | Rosenberg et al. | 601/9 |

OTHER PUBLICATIONS

Alo, "Recent Advances in Neurostimulation Analgesia," Techniques in Regional Anesthesia and Pain Management, vol. 5, No. 4, 2001, pp. 142-151.
Campanella, "Investigations of Sound Waves Generated by the Hall Effect in Electrolytes", J. Acoust. Soc. Am., vol. 111, No. 5, 2002, pp. 2087-2096.

(Continued)

*Primary Examiner*—Charles A Marmor, II
*Assistant Examiner*—Christine D Hopkins
(74) *Attorney, Agent, or Firm*—Shay Glenn LLP (57) ABSTRACT

One aspect of the invention provides a method of stimulating a nerve in tissue of a patient. The method includes the following steps: applying a focused ultrasound beam to the tissue; applying a first magnetic field to the tissue; and applying a second magnetic field to the tissue, the ultrasound beam and the first and second magnetic fields combining to stimulate the nerve. Another aspect of the invention provides a nerve stimulation device having two magnetic coils of opposite polarity each adapted to generate a magnetic field in a patient's tissue, the coils being positioned to generate a substantially toroidal magnetic field within the patient's tissue; and an ultrasound source adapted to transmit a focused ultrasound beam into the patient's tissue.

9 Claims, 5 Drawing Sheets

OTHER PUBLICATIONS

Davey et al., "Magnetic Stimulation Coil and Circuit Design," IEEE Trans. Biomed. Eng., vol. 47, No. 11, 2000, pp. 1493-1499.

Fatemi et al., "Ultrasound-Stimulated Vibro-Acoustic Spectrography," Science, vol. 280, 1998, pp. 82-85.

Fry, "Electrical Stimulation of Brain Localized without Probes R Theoretical Analysis of a Proposed Method," J. Acoust. Soc. Am., vol. 44, No. 4, 1968, pp. 919-931.

Geddes et al., Principles of Applied Biomedical Instrumentation, Third Edition, John Wiley & Sons, New York, pp. 453-491, 1989.

Grandori et al., "Magnetic stimulation of the motor cortex Theoretical considerations," IEEE Trans. Biomed. Eng., vol. 38, No. 2 1991 pp. 180-191.

Guru et al., Electromagnetic Field Theory Fundamentals, Second Edition, Cambridge University Cambridge, UK, 2004, ch. 6-7.

MacCabee et al., "Influence of pulse sequence, polarity and amplitude on magnetic stimulation of human and porcine peripheral nerve," J. Physiology, vol. 513.2, 1998, pp. 571.

Norton, "Can Ultrasound be Used to Stimulate Nerve Tissue?" Biomedical Engineering Online, (2003).

Ospina et al., "Prevalence of Chronic Pain: An Overview," Alberta Heritage Foundation for Medical Research, Health Technology Assessment, Edmonton, Alberta, Canada, 2002.

Reilly, "Peripheral nerve stimulation by induced electric currents: exposure to time-varying magnetic field," Medical and Biological Engineering and Computing, vol. 27, 1989.

Roth et al., "A Model of the Stimulation of a Nerve Fiber by Electromagnetic Induction," IEEE Trans. Biomed. Eng., vol. 37, 1990, 588-597.

Ruohonen et al., "A volume-conduction analysis of magnetic stimulation of peripheral nerves," IEEE Trans. Biomed. Eng., vol. 43, pp. 669-677 (1996).

Spinal Cord Stimulation for Neuropathic Pain, Health Technology Literature Review, Ministry of Health and Long Term Care, Toronto, Ontario, Canada, 2005.

Squire et al., Fundamental Neuroscience, Second Edition, Academic Press, Elsevier Science, San Diego CA, 2003, pp. 667-698.

Tofts, "The distribution of induced currents in magnetic stimulation of the nervous system", Phys. Med. Biol. vol. 35, 1990, 1119-1128.

Wen et al., "An Imaging Method Using the Interaction between Ultrasound and Magnetic Field," IEEE Ultrasonics Symposium, 1997, pp. 1407-1410.

\* cited by examiner

DEVICE AND METHOD FOR NON-INVASIVE, LOCALIZED NEURAL STIMULATION UTILIZING HALL EFFECT PHENOMENON

CROSS REFERENCE TO RELATED APPLICATIONS

This application claims priority under 35 U.S.C. §119 to U.S. Application No. 60/745,829, filed Apr. 27, 2006, the disclosure of which is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference

BACKGROUND OF THE INVENTION

Neuropathy and Spinal Cord Stimulation ("SCS")

Neuropathic pain is prevalent in the US in approximately 1.5% of the population, 1% in the UK, and at a comparable level in Canada ("Spinal Cord Stimulation for Neuropathic Pain, Health Technology Literature Review," *Ministry of Health and Long Term Care*, Toronto, Ontario, Canada, 2005). In 2002, it was reported that between 6 and 10 million Americans were afflicted with Neuropathic pain (P. S. Staats, "Intrathecal Therapy for Neuropathic Pain," *Proceedings of the 18th Annual Meeting of the American Academy of pain Medicine (AAPM)*, San Francisco, 2002). Neuropathic pain is generally caused by a dysfunction in the nervous system and is a known complication of diabetes mellitus, which represents 6% of the US population. About 15 percent of patients with diabetes have both symptoms and signs of neuropathy, but nearly 50 percent have evidence of peripheral nerve damage as judged by nerve conduction abnormalities (A. H. Ropper, R. H. Brown, *ADAMS AND VICTOR'S PRINCIPLES OF NEUROLOGY, Eighth Edition*, The McGraw-Hill Companies, Inc, 2005, ch.46). People suffering from neuropathic pain are generally considered to have chronic pain, which can lead to loss of productivity, depression and reduction in Quality of Life. Neuropathy presents as Failed Back Surgery Syndrome (FBSS), Complex Regional Pain Syndrome (CRPS), and postherpetic neuralgia. For each of these conditions, Spinal Cord Stimulation (SCS) is considered as a viable therapy only after failure of treatments with pharmacological, nonpharmacological and surgical treatments.

SCS systems are comprised of an implantable pulse generator and a lead with electrodes at the distal end surgically positioned in the epidural space, posterior to the spinal cord. SCS treatment is considered weakly to moderately effective in the treatment of chronic pain due to neuropathy when all else fails. SCS works by passing impulses through a nerve fiber that is either inhibiting the pain signal, or disrupting a nerve fiber that is conducting the pain signal.

SCS Limitations

For patients studied between 2000 and 2005, about 1.2% had complication due to infection and another 1.2% due to dural puncture and 11% technical failures due to electrode migration or malpositioning. Additionally, SCS electrodes used to be implanted in a less conductive medium than that of the Cerebral Spinal Fluid (CSF), percutaneously, but complications with fibrosis altered device behavior (K. M. Alo, "Recent Advances in Neurostimulation Analgesia," *Techniques in Regional Anesthesia and Pain Management*, Vol. 5, No. 4, 2001, pp: 142-151). Since the CSF is highly conductive, it acts as a shunt, requiring electrode guarding techniques and increase in number of stimulation sites to four in order to obtain adequate current focusing. This approach is highly sensitive to electrode placement due to the need to focus the electric current across the stimulated axon, and over time, the electrodes migrate in the epidural space, decreasing the effectiveness of the treatment.

Nociceptive Pain

More generally, chronic pain (CP) that is nociceptive has been poorly defined and documented until recently and is considered widely undertreated. According to the International Association for the Study of Pain (IASP), CP prevalence ranges from 10.5% to 55.2%. The American College of Rheumatology (ACR) estimated CP prevalence at 10.1% to 13%. Studies show that there is little variation of prevalence in populations, ranging from 8% in children to approximately 11% in Adults. CP is generally defined as pain that persists beyond the normal time of healing and may be associated with a disease where healing may never occur (M. Ospina and C. Harstall, "Prevalence of Chronic Pain: An Overview," *Alberta Heritage Foundation for Medical Research, Health Technology Assessment*, Edmonton, Alberta, Canada, (2002)). Different associations have generally defined CP to present as chronic if it persists beyond the range of one to six months, with many agreeing on three.

Treatment of nociceptive pain that is acute, post-surgical or chronic is generally done with analgesics. In particular, chronic pain has given rise to patient-controlled-analgesic infusion pumps (PCA's) (see U.S. Pat. No. 5,630,710), which are capped to limit amount of opiates and reduce dependency. In addition, transcutaneous electrical neural stimulators (TENS) devices (see, e.g., U.S. Pat. No. 4,121,594) demonstrated moderate impact on the suppression of pain, but were never used alone to suppress severe pain. Many TENS devices are commonly used for massage, where they pass electrical current through large muscle fiber, contracting it and in essence stimulating ascending large fiber neurons which were thought to suppress pain. SCS devices are deployed when all pharmacological solutions are exhausted in patients with intractable pain. Studies have also shown that intermittent stimulation of the spinal cord in sessions provides relief for both nociceptive and neuropathic pain, allowing of the scheduling of stimulation sessions using non-implantable subcutaneous needle electrodes.

Mechanisms of Pain

Pain, whether introduced nociceptively by tissue damage, or neuropathically by nerve damage, is conducted through the peripheral nervous system and transmitted to the spinal cord via Aδ and C-fibers. C fibers are small, non-myelenated and slow conducting in the range of 0.5-1.2 m/s. C-fiber diameter is in the order of 1 mm and has a membrane time constant of 0.25-3 ms. Some Aδ fibers are faster conducting 12-36 m/s and have membrane time constants that range to 0.1 ms (L. R. Squire, F. E. Bloom, S. K. McConnell, J. L. Roberts, N. C. Spitzer, M. J. Zigmond, *Fundamental Neuroscience, Second Edition*, Academic Press, Elsevier Science, San Diego Calif., 2003, ch. 25).

Aδ fibers, the faster conductors of pain, are carriers of the "first pain" sensation that is very highly localized. First pain is much more tolerable than the sustained second pain, and is the trigger to a reflexive withdrawal to cutaneous pricking, for instance. Aδ fibers are also mechanoceptors that respond to application of heat with very high threshold. Repeated application of heat stimuli on Aδ mechanoceptors receptor sites decreases the threshold, increases the response, thus leading to sensitization.

C fibers are polymodal, responding to tissue deformation, noxious stimuli and heat. They are responsible for the second pain which is poorly localized and poorly tolerated. In general, they transmit burning sensations. Aβ fibers are larger mechanoceptors, synapsing more anteriorly within the spinal cord to Aδ and C fibers. These larger fibers are considered by some researchers to be responsible for the "Gate Control Theory," where their stimulation is responsible for neuromodulation, or suppression, of pain sensation in the smaller fiber group. Many have refuted this finding, yet it is known that muscle contraction of pain-sites using TENS devices decreases pain response and provides prolonged relief.

Neuromagnetic Stimulation

Devices and methods for performing neurostimulation using a combination of a magnetic field and ultrasound have been described. See., e.g., U.S. Pat. No. 5,476,438. Such systems purport to stimulate nerves by applying a magnetic field generally to the nerve and simultaneously focusing an ultrasound beam on the nerve.

SUMMARY OF THE INVENTION

The present invention relates to a device and method for non-invasive stimulation of nerves for, e.g., treating pain, controlling nerve function or performing mapping studies. In some aspects, the present invention relates to devices and methods that stimulate nerves non-invasively within the human body, and more particularly, Aδ-fibers and C-fibers for pain control, with improvements on Transcutaneous Electrical Nerve Stimulation (TENS); spinal cord stimulation (SCS) for inducing anesthesia and controlling pain; any deep-brain stimulation (DBS) including any part of the cortex, hippocampus, basal ganglia, the subthalamic nucleus, the caudate and the dentate; pudendal nerve for controlling urinary incontinence; and the vagal nerve for inducing parasympathetic modulation. Some aspects of the method relate to improved non-invasive stimulation of any target site, nerve or muscle that is deeply or superficially located utilizing localized Hall Effect phenomenon. The device induces Hall Effect stimulation by combining ultrasound delivered by an external transducer, with a magnetic fields delivered by external electromagnets, boosted by a subthreshold electric field delivered transcutaneously utilizing surface electrodes.

The device and method of this invention may be used for the following indications: post-surgical acute pain, nociceptive acute and chronic pain, neuropathic chronic pain, localized anesthesia, and substitute for epidural during surgery and caesarian delivery. The device could be used in conjunction with analgesics to reduce dosage of barbiturates and long-term dependency on opiates.

In another aspect of this invention, the device and method may be used by neurosurgeons for brain mapping prior to permanent implantation of deep-brain stimulator (DBS) devices. DBS is indicated for the control of: epilepsy, Parkinson's disease, Essential Tremor, severe migraines, phantom limbs and chronic pain, depression, dementia due to Alzheimer's and other intractable conditions requiring technological and surgical interventions. In current procedures, following MRI, stereotactic intraoperative mapping is employed to localize DBS targets while the skull is open and the patient is awake, providing psychophysical and instrumented feedback. The results of such procedures are often suspect since drugs are used to block patient pain throughout the procedure, present a transient response, compounded by the presence of a single-unit mapping electrode. Permanent electrode target localization is a lengthy process that requires multiple insertions of single-unit electrodes through a cannula. Repeated insertions of mapping electrodes are known to produce nerve damage in the insertion path. Using this invention, mapping is conducted prior to operating, without the insertion of the mapping electrode, thereby allowing the neurosurgeon to reduce or eliminate intraoperative brain mapping prior to permanent electrode placement and test stimulation parameters of DBS devices to determine in advance the efficacy of such technological interventions.

In another aspect, the device and method of this invention are intended for stimulation-induced lipolysis for regulation of long-term energy balance cycle in obese patients. The preferred target is the lateral cutaneous femoral nerve. Such use may supplement future implanted obesity devices that focus on short-term satiety measures, but do not address endocrine modulators such as leptin, that may relate to suppression of natural lipolysis in morbidly obese patients.

In yet another aspect of this invention, the device and method serve as research tools for new implantable stimulators intended for nerve or muscular targets, for, e.g., the control of urinary incontinence by targeting the pudendal nerve, obesity by targeting the vagus nerve or nerves controlling intestinal peristalsis, and other systemic endocrine processes regulated by the autonomic nervous system that may benefit from such non-invasive stimulation. The research devices would allow clinicians and regulating agencies to determine prior to implantation whether permanent implants would result in favorable outcomes.

Mechanism of Stimulation

The mechanism of stimulation utilizes the superposition of electric currents introduced by the following electric field sources:

(1) Hall Effect due to the interaction of Ultrasound and Magnetic Fields (see, S. J. Norton, "Can Ultrasound be Used to Stimulate Nerve Tissue?" *Biomedical Engineering Online*, (2003); Angelo Campanella, "Investigations of Sound Waves Generated by the Hall Effect in Electrolytes", *J. Acoust. Soc. Am.*, Vol 111, No.5, 2002, pp. 2087-2096; H. Wen, E. Bennett, J. Shah, R. S. Balaban, "An Imaging Method Using the Interaction between Ultrasound and Magnetic Field," *IEEE Ultrasonics Symposium*, 1997, pp. 1407-1410);

(2) Magnetic induction of electric current due to oscillating magnetic fields, as is the case with coil electrodes or Transcranial Magnetic Stimulation (TMS) (see, W. J. Fry, "Electrical Stimulation of Brain Localized without Probes—Theoretical Analysis of a Proposed Method," *J. Acoust. Soc. Am.*, Vol 44, No.4, 1968, pp. 919-931; Ruohonen, P. Ravazzani, J. Nilsson, M. Panizza, F. Grandori, G. Tognola, "A volume-conduction analysis of magnetic stimulation of peripheral nerves," *IEEE Trans. Biomed. Eng.*, vol. 43, pp. 669-677 (1996); K. Davey, C. M. Epstein, "Magnetic Stimulation Coil and Circuit Design," *IEEE Trans. Biomed. Eng.*, Vol. 47, No. 11, 2000, pp. 1493-1499; F. Grandori, P. Ravazzani, "Magnetic stimulation of the motor cortex-Theoretical considerations," *IEEE Trans. Biomed. Eng*, Vol. 38, No.2 1991 pp. 180-191; B. J. Roth et al., "A theoretical calculation of the electric field induced in the cortex during magnetic stimulation," *Electroencephalography and Clinical Neurophysiology*, Vol. 81, 1991, pp. 47-56); and (3) Transcutaneous Electrical Neural Stimulation (TENS) devices.

This invention entails localization of electric fields via spatial focusing of power over a small biological target. The spatial focusing is limited only by the wavelength of the ultrasonic wave and, in the presence of a magnetic field, creates a Lorentz Force in an electrolytic medium. The induced current due to the Lorentz Force (see, B. S. Guru, H. R. Hiziroglu, *Electromagnetic Field Theory Fundamentals, Second Edition*, Cambridge University Cambridge, UK, 2004, ch. 6-7) is:

$$\vec{J} = \sigma \vec{v} \times \vec{B} \qquad (1)$$

where,

J is the current density vector in A/m$^2$,

σ is the conductivity of tissue in S/m, v is the velocity of particle motion due to the ultrasonic wave pressure in m/s, and B is the magnetic flux density in T.

Current traveling through a coil activates the magnetic field. The coil may be wound on a ferromagnetic core (or a similar magnetic material, such as an iron-cobalt alloy) to enhance the magnetic field, or could be a simple set of wire loops without any core. The magnetic field oscillates at a frequency that is equal or less than that of the ultrasound, and could theoretically be a constant DC field. Oscillating magnetic field amplitudes within the range of 0-3 T may be generated, and for practical reasons, dampened sinusoids or pulses are selected. This disclosure, however, covers any frequency or amplitude sufficient to introduce an incremental Hall Effect electric field sufficient to stimulate tissue.

A secondary effect of oscillating magnetic fields is an induced current density in the conductive tissue, which is derived from Faraday's induction law and Lenz's law, is described below:

$$\vec{J} = \sigma \vec{E} = \sigma \left( K \frac{d\phi}{dt} \right) = \sigma K \mu N \left( \frac{dI}{dt} \right) \int_A d\vec{s} \qquad (2)$$

where,

J is the current density vector in A/m$^2$,

E is the electric field in V/m,

σ is the conductivity of tissue in S/m,

K is the effective mutual inductance between the coil and the biological medium, Φ is the magnetic flux through the coil N is the number of turns on the coil, I is the current in the coil windings, ds is an element of the cross-sectional area of the electromagnet producing the coupled magnetic field, and μ is the core permeability.

This current is much less localized than that of the one induced by the Hall Effect phenomenon, yet it provides a subthreshold component to which the Hall Effect current is added. This generalized current could play an important role in lowering the total required energy delivered by ultrasonic stimulation and is an added benefit of using switched oscillating current to achieve the desired magnetic field strengths required for the Localized Hall Effect of this invention to operate. Many published simulations using the Hodgkins-Huxley model have shown that nerve stimulation would occur in induced electric fields ranging from 6 V/m–100 V/m (see, e.g., F. Grandori, P. Ravazzani, "Magnetic stimulation of the motor cortex—Theoretical considerations," *IEEE Trans. Biomed. Eng.*, Vol. 38, No.2 1991 pp. 180-191; J. P. Reilly, "Peripheral nerve stimulation by induced electric currents: exposure to time-varying magnetic field," *Medical and Biological Engineering and Computing*, Vol. 27, 1989, 101-110; P. Tofts, "The distribution of induced currents in magnetic stimulation of the nervous system", Phys. Med. Biol. Vol. 35, 1990, 1119-1128; P. J. Maccabee, S. S. Nagarajan, V. E. Amassian, D. M. Durand, A. Z. Szabo, A. B. Ahad, R. Q. Cracco, K. S. Lai, L. P. Eberle, "Influence of pulse sequence, polarity and amplitude on magnetic stimulation of human and porcine peripheral nerve," *J. Physiology*, vol. 513.2, 1998, pp. 571-585; B. J. Roth, P. J Basser, "Model of the Stimulation of a Nerve Fiber by Electromagnetic Induction," *IEEE Trans. Biomed. Eng*, vol. 37, 1990, 588-597). Based on experience, adequate recruitment in the cortex with invasive electrodes requires around 100 V/m at frequencies exceeding that of the membrane time constant requirements and is estimated to be significantly less in large myelinated nerves.

The third component in this approach entails the widely utilized concept of Transcutaneous Electric Neural Stimulation (TENS), introduced by surface electrodes. The surface electrodes are needed only in some cases and provide a baseline electric current component, which is non-localized, at a subthreshold level. The addition of all three currents provides deep neural stimulation of any targeted axon with electric field gradients that are dictated by the wavelength of the ultrasonic carrier frequency.

Hall Effect generation of Lorentz forces was successfully demonstrated by Wen for use as a novel imaging modality, called Hall Effect Imaging (HEI). For imaging, the reverse approach is applied where large pulses of electric field are generated across an electrolytic medium, resulting in pressure waves. The strength of the resultant ultrasonic source is proportional to the electrical conductivity of the medium. The ultrasonic wave is then detected by a hydrophone. In this way, an image of tissue conductivity can be built up.

Ultrasound Demodulation and Wave Interaction

High spatial resolution requires high-frequency ultrasound, resulting in small wavelengths. In DBS applications, spatial separation between electrodes is in the order of 1-5 mm. The Hall Effect phenomenon generates electric fields that are at the same frequency of ultrasound within a DC, or a much slower oscillating magnetic field. To obtain high spatial resolution, an ultrasound frequency on the order of several hundred kHz to MHz or above is required, depending on the clinical application.

Non-destructive amplitudes for nerve stimulation tend to be at periods close to the natural membrane time constant and shown repeatedly in the literature on strength duration curves (see L. A. Geddes, L. E. Baker, *Principles of Applied Biomedical Instrumentation, Third Edition*, John Wiley & Sons, New York, 1989). Such periods equate to frequencies of 1-10 kHz for SCS and DBS applications.

Fatemi and Greenleaf published a breakthrough discovery in 1998 documenting that MHz-frequency ultrasound could be utilized to measure elasticity and other mechanical characteristics of biological targets, that have natural frequencies that are orders of magnitude lower than those of the carrier signals. (See M. Fatemi, J. F. Greenleaf, "Ultrasound-Stimulated Vibro-Acoustic Spectrography," *Science*, VOL. 280, 1998, pp. 82-85.) The concept involves two incident waves, at slightly different frequencies, introduced by con-focal ultrasonic transducers, and later by sector arrays (see G. T. Silva, S. Chen, A. C. Frery, J. F. Greenleaf, M. Fatemi, "Stress Field Forming of Sector Array Transducers for Vibro-Acoustography," *IEEE Transactions on Ultrasonics, Ferroelectrics, and Frequency Control*, 2005, vol. 52, no. 11, pp. 1943-1951). The two co-incident waves interact in a non-linear manner and produce a detectable sonic wave at the difference frequency. Their imaging method is called vibro-acoustography and was demonstrated as useful in the detection of breast cancer, since tumors have different mechanical characteristics than the surrounding tissue.

The device disclosed herein uses difference frequency approaches to demodulate MHz-range ultrasound in some embodiments for stimulation purposes. The difference frequency method will allow the generation of 1-10 kHz electric field potential, transmitted deep into the body and modulated by two co-incident ultrasonic sources operating in the MHz range.

Neural Stimulation using Hall Effect

As indicated earlier, the device and method of this invention has three components to its current, added with superposition:

(1) Current due to the Hall Effect localized at a small target region within an ultrasonic wavelength and perpendicular to the magnetic field. The current may be induced at the fundamental frequency of the ultrasound with long wavelengths, or at difference frequencies from two separate sources. We define the current density due to Hall Effect as $\vec{J}_{HE}$.

(2) Current inducted by Lenz's and Faraday's laws due to the use of oscillating magnetic fields, since large magnetic fields created by DC current in the windings may be impractical. We refer to current density due to magnetic oscillation as $\vec{J}_{mg}$.

(3) Current conducted by the application of electrodes around the stimulation site utilizing TENS. We refer to current density due to surface electrodes as $\vec{J}_{SE}$.

The total current density is therefore, $$\vec{J}_{TOT} = \vec{J}_{HE} + \vec{J}_{mg} + \vec{J}_{SE}. \quad (3)$$

$\vec{J}_{HE}$ is defined in equation (1) and $\vec{J}_{mg}$ is defined in equation (2) above. The current density between two electrodes, positioned on the z-axis, with separation distance, d, and current, I, obeys Laplace's equation and is represented as:

$$\vec{J}_{SE}(0, 0, z) = \frac{I}{4\pi}\left[\frac{1}{\left(z+\frac{d}{2}\right)^2} + \frac{1}{\left(z-\frac{d}{2}\right)^2}\right]\hat{z}. \quad (4)$$

The final component is the Hall Effect current density, derived from equation (1) above, and assuming a magnetic field that is perpendicular to the propagation of ultrasound, it can be expressed in scalar form as:

$$J = \sigma v B. \quad (5)$$

Let the particle velocity function be a sinusoid with frequency, $\omega_a$, wave constant, k, and peak velocity $v_0$, then time-averaged J along the x-axis is expressed as:

$$J(x) = \frac{\sigma}{T}\int_0^T V_0 \sin(\omega_a t - kx) B(t) dt \quad (6)$$

One embodiment of the device of this invention operates in a manner such that $\vec{J}_{HE}$ is direct current (DC). We can obtain DC current density by setting $B(t)=\sin(\omega_a t)$, in which case (6) becomes:

$$J_{dc}(x) = \frac{1}{2}\sigma v_0 B_0 \cos(ikx) \quad (7)$$

The DC current may be turned on and off to achieve optimal modulation or pulse train stimulation.

In another embodiment, a current density oscillating at a low frequency (rather than DC) can be achieved by varying the magnetic field at a slighting different frequency than the ultrasonic frequency. In this case, one sets $B(t)=\sin((\omega_a+\Delta\omega)t)$. Using this in Eq. (6) gives a current density similar to Eq. (7), but with a temporal modulation at the frequency $\Delta\omega$. This frequency could be selected for optimal stimulation (e.g., approximately 10 kHz).

One aspect of the invention provides a method of stimulating a nerve in tissue of a patient. The method includes the following steps: applying a focused ultrasound beam to the tissue; applying a first magnetic field to the tissue; and applying a second magnetic field to the tissue, the second magnetic field differing from the first magnetic field, the ultrasound beam and the first and second magnetic fields combining to stimulate the nerve. In some embodiments, the nerve is in a dorsal spinal root or dorsal column, and in such embodiments the method could includes the step of stimulating the nerve to treat pain. In some embodiments the nerve is a peripheral nerve, and in such embodiments the method could include the step of controlling the function of the peripheral nerve. In some embodiments the nerve is in the deep brain, and in such embodiments the method could include the step of stimulating the nerve to perform a mapping study.

In some embodiments, the first magnetic field is a DC field. In other embodiments, the step of applying a first magnetic field includes the step of pulsing or oscillating the first magnetic field at a frequency from, e.g., about 0.5 Hz to about 300 Hz.

In some embodiments, the step of applying a first magnetic field includes the step of applying the first magnetic field at a first polarity and the step of applying a second magnetic field includes the step of applying the second magnetic field at a second polarity opposite to the first polarity. In other embodiments, the first and second magnetic fields are applied at the same polarity. The first and second magnetic fields may generate a substantially toroidal magnetic field in the tissue. In some embodiments, the spacing between first and second magnetic fields sources may be changed.

In some embodiments, the method includes the step of applying an electric voltage, or controlled current, to a surface of the tissue (such as, e.g., the patient's skin) using electrodes that are spaced apart from the nerve yet create electric fields that encompass the nerve. In such embodiments, an electrode may be adhered to the tissue surface. The electric field may be applied with a TENS device and may be applied to the nerve may be less than a stimulation threshold for the nerve.

In some embodiments, the step of applying a focused ultrasound beam includes the step of applying a continuous wave ultrasound beam. In other embodiments, the step of applying a focused ultrasound beam includes the step of applying a pulsed ultrasound beam. In some embodiments a second focused ultrasound beam is applied to the tissue, and the first and second ultrasound beams may be at different frequencies.

Yet another aspect of the invention provides a method of stimulating a nerve in tissue of a patient, the method including the steps of applying a focused ultrasound beam to the tissue; applying a first magnetic field to the tissue; applying a second magnetic field to the tissue; and applying an electric field to a tissue surface spaced apart from the nerve (such as a skin surface), the ultrasound beam, the first and second magnetic fields and the electric field combining to stimulate the nerve. In some embodiments, the electric field is applied with a TENS device.

Another aspect of the invention provides a nerve stimulation device having two magnetic coils of opposite polarity each adapted to generate a magnetic field in a patient's tissue, the coils being positioned to generate a substantially toroidal magnetic field within the patient's tissue; and an ultrasound source adapted to transmit a focused ultrasound beam into the patient's tissue. In some embodiments, the device also includes a first electrode adapted to be applied to a surface of the patient's tissue and a power source adapted to provide a voltage between the first electrode and a second electrode. The device may also include a controller adapted to control the voltage and/or current between the electrodes.

In some embodiments, the device has a second ultrasound source adapted to transmit a focused ultrasound beam into the patient's tissue. In some embodiments, the device includes a controller adapted to control operation of the magnetic coils and the ultrasound source. The controller may include a user control adapted to adjust an operation parameter of at least one of the magnetic coils and the ultrasound source.

Further details of the device and method of the invention will be described with reference to the drawings.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
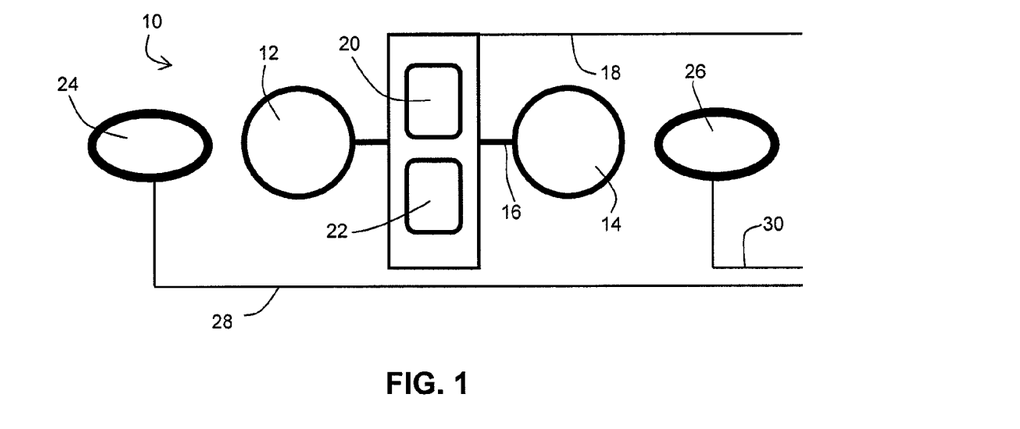
FIG. 1 is a schematic drawing of a patient/device interface according to one embodiment of the invention.

FIG. 1 shows schematically an interface between a stimulation device and a patient. The interface 10 has two magnetic coils 12 and 14 with opposite polarity which together generate a magnetic field in the shape of a torus. In this embodiment, the distance between the two magnetic coils may be varied as desired. In other embodiments, the distance between the magnetic coils may be fixed. Coils 12 and 14 connect to a controller (not shown) via conductors 16 and a conduit 18. In use, coils 12 and 14 may be adhered to the skin or other tissue surface of the patient.

One or more ultrasound sources are disposed in the center of interface 10. In some embodiments, the ultrasound sources will be focused on the axon of interest to create a Hall Effect current. The ultrasound source may be a single transducer, a con-focal transducer, two separate transducers, or two separate arrays operating at slightly different frequencies, with a resultant wave at the difference frequency representing the stimulation profile. The embodiment shown in FIG. 1 employs two ultrasound sources, 20 and 22, connected to the controller via conduit 18. Holes (not shown) may be provided beneath the ultrasound sources to provide room for gel application. In use, the ultrasound sources may be adhered to the patient's skin or other tissue surface.

This embodiment also uses surface electrodes 24 and 26 to add a baseline electric field in order to decrease the stimulation amplitudes required by the localized Hall Effect phenomenon. Electrodes 24 and 26 communicate with the controller via conductors 28 and 30, respectively. In use, these surface electrodes are adhered to the patient's skin or other tissue surface and may use conductive gel to create electric current uniformity at the electrode/tissue interface.

Figure 2:
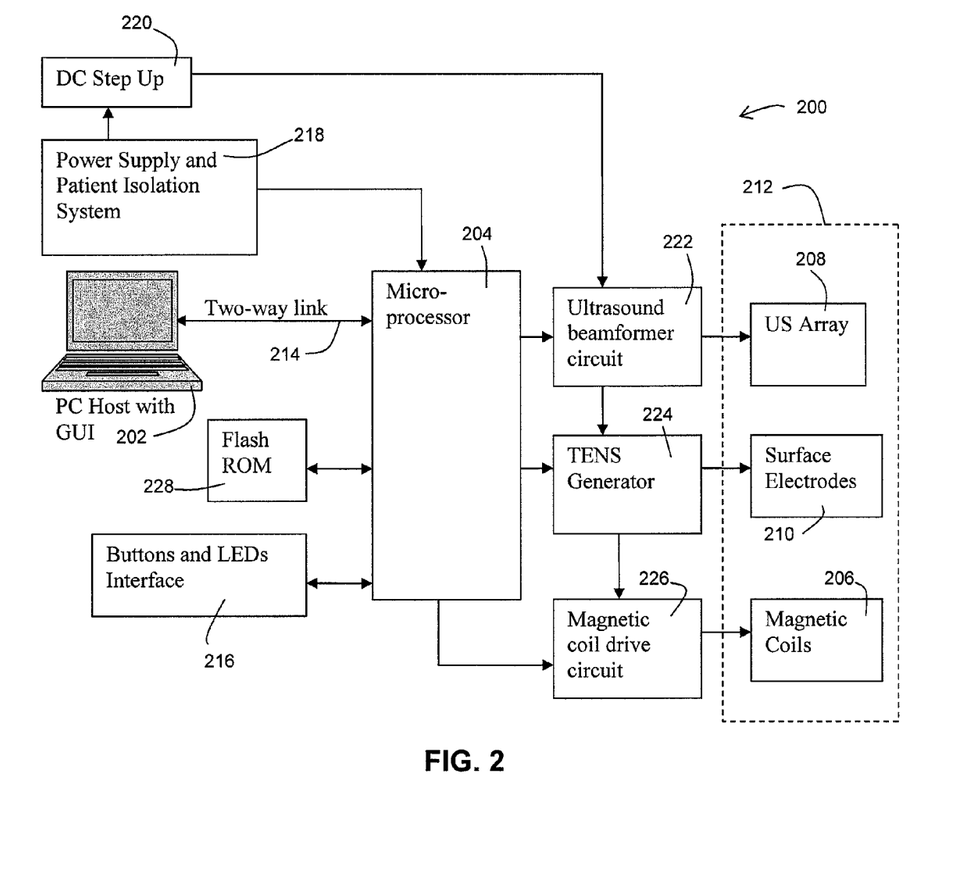
FIG. 2 shows the architecture of a stimulator system according to one embodiment of the invention.

FIG. 2 shows the architecture of a stimulator system 200 according to one embodiment of the invention. The device architecture is that of a host-controller model. The host 202 provides a user interface allowing the clinician to alter stimulation parameters for the magnetic coils 206, the ultrasound sources 208, and the transcutaneous electrodes 210 comprising the patient interface 212. The host is comprised of software running on a personal computer. The controller 204 is an embedded processor, interfaced with the host via a communication port 214, with a processor that controls each of the three modalities. Once the stimulation parameters are downloaded, the host 202 and controller 204 could be disconnected. A simple user interface 216 is provided via buttons and LEDs on the controller front panel.

Other elements of the system of this embodiment include a power supply 218, a DC step up 220, an ultrasound beamformer circuit 222, a TENS generator 224, a magnetic coil drive circuit 226 and flash ROM 228.

Figure 3:
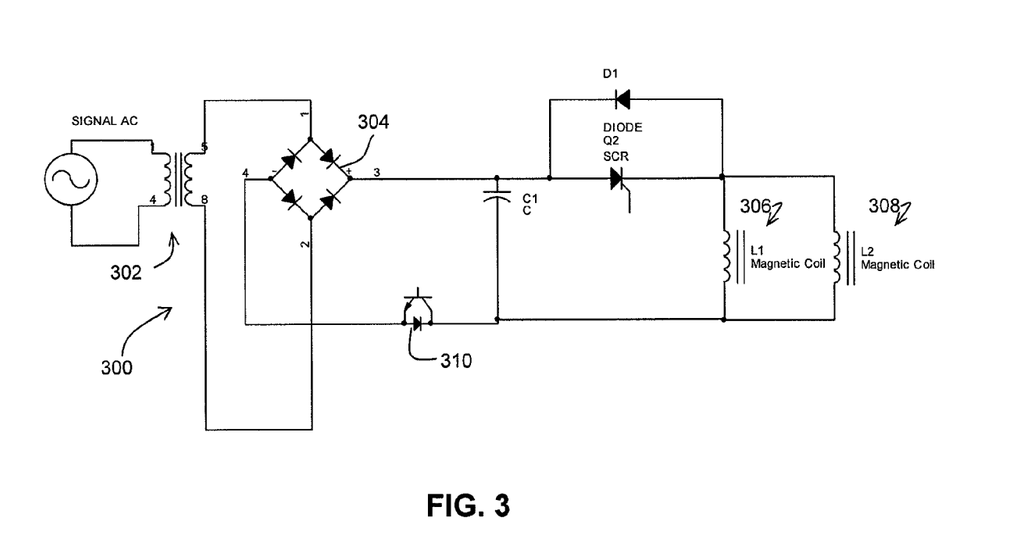
FIG. 3 is a schematic drawing of a magnetic coil drive circuit for use with this invention.

In one embodiment, shown in FIG. 3, the magnetic coil drive circuit 300 is a simple DC charge capacitor circuit powered by a step-up transformer 302 via a full-wave rectifier 304. The two coils 306 and 308 are powered via a silicone controlled rectifier (SCR) which discharges the capacitor into the windings of the coils. The coils may possibly be wound around a ferromagnetic core to enhance the field strength, or could simply be a wire loop with multiple turns. The ferromagnetic core may have any shape such that the flux at its end or side is optimized for the clinical application. The microprocessor allows the circuit to oscillate once at its natural frequency using the SCR and another transistor switch 310. The voltage source, not shown in this figure, is an amplified voltage controlled oscillator driven by a digital potentiometer that the microprocessor programs through a serial connection.

Figure 4:
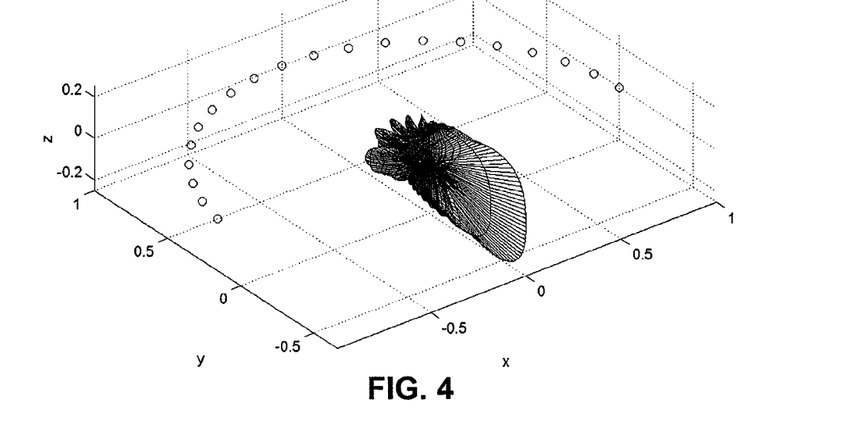
FIG. 4 is a computer-generated representation of an ultrasound array factor suitable for use with this invention.

Up to two ultrasonic beamformers could be used in this device, and as few as one transducer depending on the clinical application. In one embodiment, each beam former is operating at a slightly different frequency than the other. As documented earlier by Fatemi and Greenfield, the interaction of the two co-incident waves results in a third wave generated non-linearly at the difference frequency. There is a fourth wave that is not of interest to this application oscillating at the sum of the two frequencies. A typical array factor pointing at 180 degrees is shown in FIG. 4. The image was generated in MATLAB from 20 different elements, simulating a phased-array antenna. Other embodiments of this invention may produce an array factor that is different than the one shown in FIG. 4.

Figure 5:
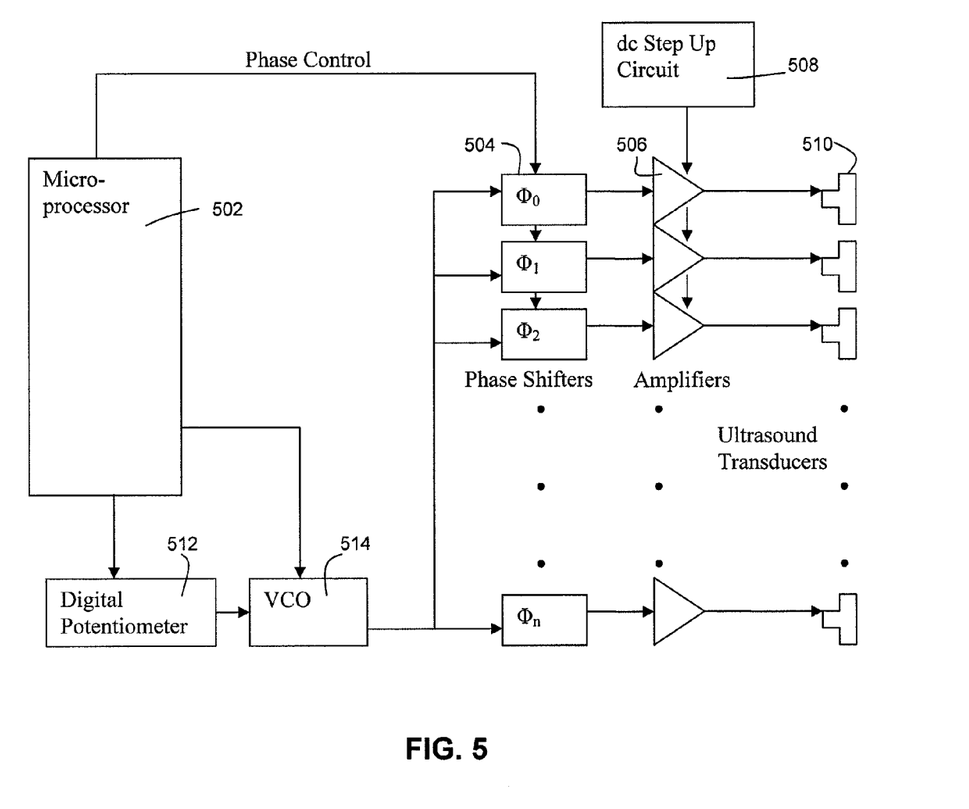
FIG. 5 is a block diagram showing beam forming architecture for use with this invention.

Beam forming architecture is shown in the block diagram shown in FIG. 5. In this embodiment, the beam forming architecture includes a microprocessor 502 providing phase control to a series of phase shifters 504, the output of which are amplified with amplifiers 506, which are connected to a DC step up circuit 508 to power the ultrasound transducers 510. A digital potentiometer 512 operating with a VCO 514 provide the raw signals driving each of the transducers and processed by the phase shifter block.

The ultrasound sources are intended to operate in continuous wave mode, thus justifying the use of programmable phase shifters. In another embodiment, pulsed ultrasound may also be used to generate a dampened sinusoidal response. With pulsed ultrasound, the microprocessor drives the transducers through an array of FET push-pull transistor-pairs, with each pulse delayed as a function of the transducer phase angle.

The third modality of the device of this invention is that of the transcutaneous neural stimulator. As mentioned earlier, this modality is only used to provide subthreshold stimulation, aiding the Hall Effect to trigger action potentials in the targeted axons. In DBS applications, for example, the use of surface electrodes may generate undesirable outcomes, while in spinal cord and peripheral applications, it may be programmed in a complex manner to exhibit a variety of neuromodulation mechanisms.

The surface electrodes could produce a variety of waveforms commonly used in neural stimulation, such as trapezoidal, asymmetric, and half-wave. The waveforms are generated by the host and downloaded into memory. The microcontroller reads the digitized waveforms, converts them to analog and sends them to the electrode pair, via current-controlled amplifiers.

Figure 6:
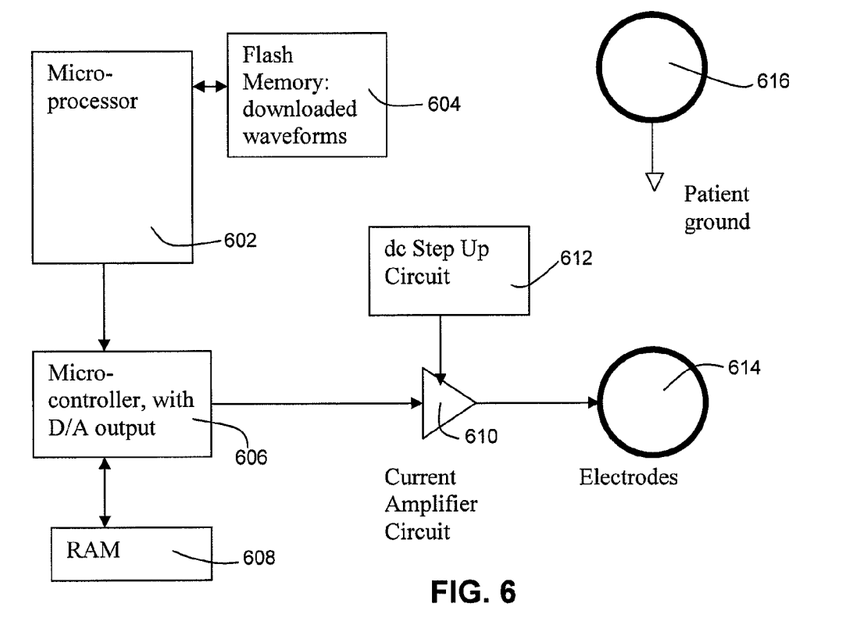
FIG. 6 is the block diagram of a TENS drive circuit for use with this invention.

FIG. 6 shows the block diagram of a TENS drive circuit. In this embodiment, a microprocessor 602 obtains waveforms from flash memory 604. A microcontroller 606 (possibly communicating with RAM 608) provides the current waveform to the electrodes 614 through an amplifier 610 and DC step up circuit 612. A separate patient ground 616 may also be provided. In another embodiment, isolation transformers or push-pull mechanisms are used to activate the surface electrodes.

In operation, the system is first set up by connecting the three major modules together: the device to the PC-host and the device to the patient-interface module. Both device and host are powered up, and the Graphical User Interface (GUI) software is run on the PC-host. The GUI contains a mathematical model that estimates magnetic induced current density due to magnetic coil operating parameters. The following parameters are then set for the magnetic drive circuit shown in FIG. 3:

(1) Amplitude of input voltage (Amc);
(2) Frequency of input voltage (Fmc);
(3) Discharge output voltage (Vo); and
(4) Discharge repetition rate (DRR).

Both Amc and Fmc influence the operation of the charging circuit and are limited by a model of that circuit for optimal and safe operation. Vo and DRR determine the physiologic response to the magnetic coils. Larger Vo results in larger coil currents, thus introducing larger fluctuation in magnetic flux. The induced current in the target membrane is proportional to dB/dt. DRR determines the steady-state response of the axon, and may result in the following physiologic effects: (1) subthreshold stimulation; (2) hyperpolarization; and/or (3) sensitization. The preferred operation of the system is the first response so that subthreshold non-localized stimulation of many nerves in the magnetic field is aided by an incremental addition of the Hall Effect voltage introduced by the ultrasound sources at the target.

Figure 7:
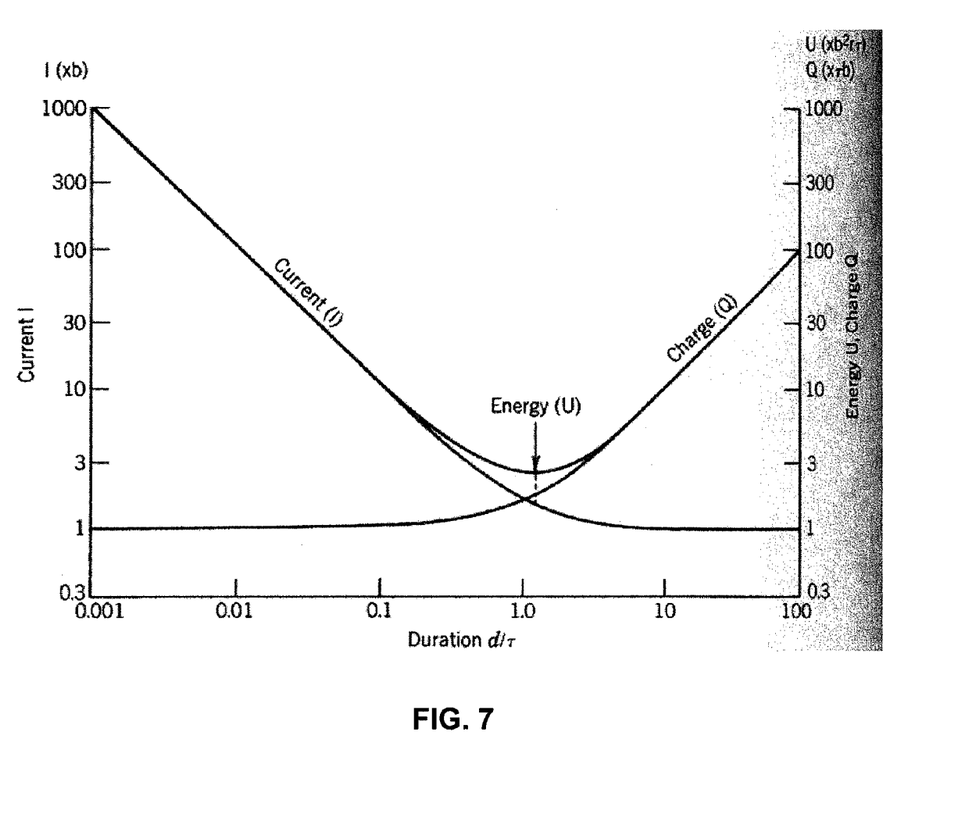
FIG. 7 shows strength duration curves for nerve stimulation.

Next, the ultrasound sources are programmed for continuous operation. In one embodiment, a single ultrasound source operates at a stimulation frequency much greater than the fluctuation frequency of the magnetic flux density, but is considered effective for the targeted axon according to the nerve stimulation strength-duration curve shown in FIG. 7.

In another embodiment, two ultrasound sources, whether single element or phased arrays, are programmed to operate at a wavelength that achieves desired localization. Ultrasound propagating in an axis transverse to that of the magnetic field, as shown in equation (1), will introduce a Hall Effect electric current. This localized phenomenon acts similar to a physical electrode, referred to herein as a "virtual electrode." The two sources operate at slightly different frequencies, and the difference of the two is the stimulation frequency determined by the strength-duration curve shown in FIG. 7.

Depending on the clinical application, stimulation sites may be too responsive to the induced current by the magnetic coils, thus requiring a decrease in flux density to a point where the Hall Effect voltage strength becomes less dominant. This situation may require the assistance of another subthreshold stimulation source, generated by the surface electrodes shown in FIG. 1. The next step in setting up the device would be to program the stimulation current in these electrodes according to a predetermined mathematical model, such that the total current due to the surface electrodes and those of the magnetic coils result in the desired non-localized physiologic effect. The added current by the Hall Effect phenomenon resulting from ionic disturbance in the magnetic field by the ultrasound pressure waves induces the incremental effect of stimulation, only at the target site within the mentioned "virtual electrode" target region.

What is claimed is:

1. A method of stimulating a nerve in tissue of a patient, the method comprising:
    applying a focused ultrasound beam to the tissue;
    applying a first magnetic field to the tissue;
    applying a second magnetic field to the tissue, the second magnetic field differing from the first magnetic field, the ultrasound beam and the first and second magnetic fields combining to stimulate the nerve; and
    applying an electric field to a surface of the tissue spaced apart from the nerve.

2. The method of claim 1 further comprising adhering an electrode to the tissue surface.

3. The method of claim 1 wherein the tissue surface is a skin surface.

4. The method of claim 3 wherein the step of applying an electric field comprises using a TENS device to apply an electric field to the skin surface.

5. The method of claim 1 wherein the step of applying an electric field comprises applying an electric field to the nerve less than a stimulation threshold for the nerve.

6. A method of stimulating a nerve in tissue of a patient, the method comprising:
    applying a focused ultrasound beam to the tissue;
    applying a first magnetic field to the tissue;
    applying a second magnetic field to the tissue; and
    applying an electric field to a tissue surface spaced apart from the nerve,
    the ultrasound beam, the first and second magnetic fields and the electric field combining to stimulate the nerve.

7. The method of claim 6 wherein the tissue surface is a skin surface.

8. The method of claim 7 wherein the step of applying an electric field comprises using a TENS device to apply an electric field to the skin surface.

9. The method of claim 1 wherein the ultrasound beam and the first and second magnetic fields combine to generate a Hall Effect electric current to stimulate the nerve.

* * * * *